Figure 1:
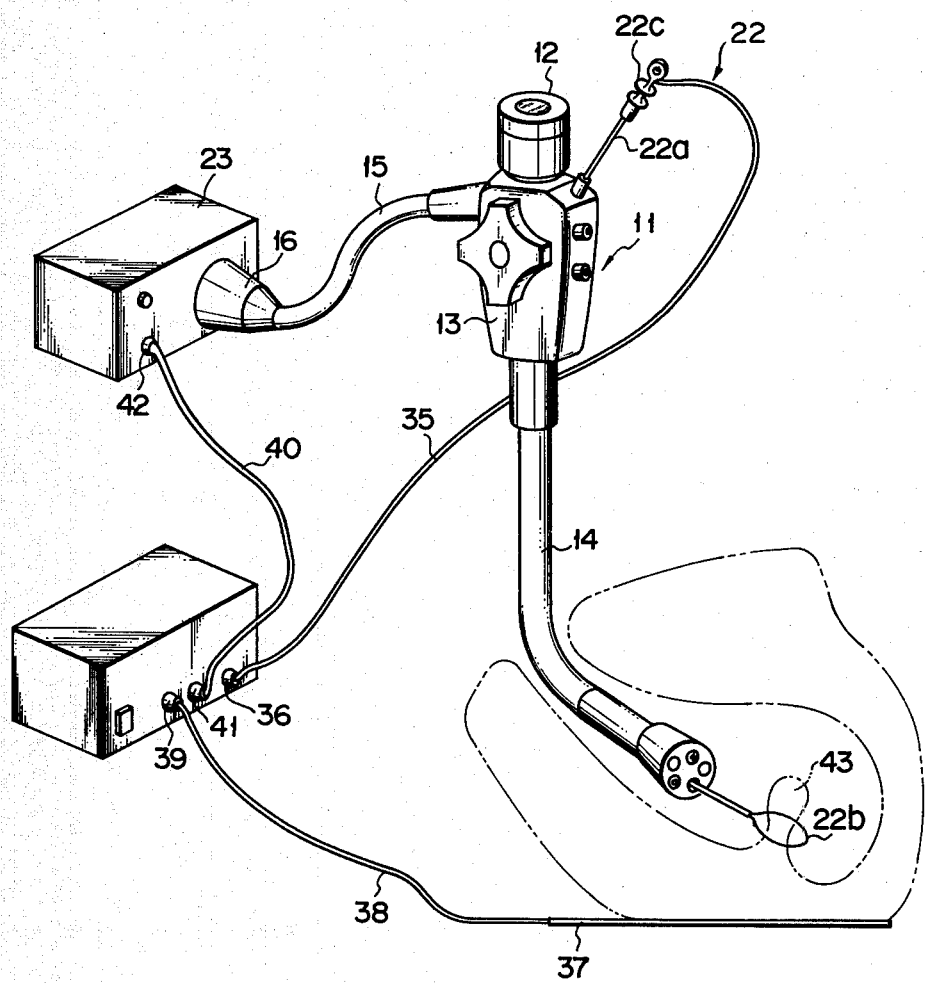

United States Patent [19]

Hagiwara

[11] 4,374,517

[45] Feb. 22, 1983

[54] ENDOSCOPE TYPE HIGH FREQUENCY SURGICAL APPARATUS

[75] Inventor: Toshihiko Hagiwara, Hino, Japan

[73] Assignee: Olympus Optical Co., Ltd., Tokyo, Japan

[21] Appl. No.: 269,875

[22] Filed: Jun. 3, 1981

[30] Foreign Application Priority Data

Jun. 10, 1980 [JP] Japan .......................... 55-79870[U]

[51] Int. Cl.³ ............................................. A61B 1/06
[52] U.S. Cl. ........................................ 128/6; 128/8; 128/303.15
[58] Field of Search ................. 128/6, 303.14, 303.15, 128/303.17, 908

[56] References Cited

U.S. PATENT DOCUMENTS

| | | | |
|---|---|---|---|
| 3,858,586 | 1/1975 | Lessen | 128/6 |
| 4,094,320 | 6/1978 | Newton et al. | 128/303.14 |
| 4,184,492 | 1/1980 | Meinke et al. | 128/303.14 |
| 4,311,143 | 1/1982 | Kemiya | 128/303.15 |

FOREIGN PATENT DOCUMENTS

| | | | |
|---|---|---|---|
| 1485423 | 6/1967 | France | 128/6 |
| 56-26497 | 4/1981 | Japan | 128/6 |

Primary Examiner—Kyle L. Howell
Assistant Examiner—Max F. Hindenburg
Attorney, Agent, or Firm—Frishauf, Holtz, Goodman and Woodward

[57] ABSTRACT

An endoscope type high frequency surgical apparatus wherein a high frequency current feedback pin is mounted on a connector of an endoscope in electrical connection to a metal section of the endoscope and also detachably connected to a feedback terminal of a light source unit; and said feedback terminal is connected to a patient output terminal of a high frequency power supply source through a feedback line.

4 Claims, 2 Drawing Figures

ENDOSCOPE TYPE HIGH FREQUENCY SURGICAL APPARATUS

This invention relates to an endoscope type high frequency surgical apparatus which treats a coeliac affected portion by high frequency current by means of an endoscope.

A high frequency surgical apparatus combined with an endoscope has hitherto been used to treat a coeliac affected portion. This high frequency surgical apparatus is provided with a safety arrangement to prevent a coeliac tissue from being burnt by high frequency current leaking from the apparatus to the endoscope. According to this safety arrangement, the metal section of an endoscope is connected to the patient output terminal of a high frequency surgical apparatus, and leaking high frequency current is returned to the patient output terminal. With the prior art high frequency surgical apparatus, the connector of the endoscope light guide cable is provided with a contact through which to return the leaking high frequency current to the patient output terminal of the surgical apparatus. This contact is detachably connected to the high frequency surgical apparatus by a feedback cord. With this prior art arrangement, the feedback cord and connector and/or high frequency surgical apparatus had to be connected to or disengaged from a light supply unit, each time the endoscope connector was connected to or detached from the light supply unit. Where, therefore, an endoscope was exchanged for another type, then the connection and detachment of both endoscope connector and feedback cord had to be undertaken. Consequently, the handling and operation of a high frequency surgical apparatus for an endoscope involved troublesome work. Further, the operator seldom forgot to connect the endoscope connector to a light supply unit, but often neglected the connection of the feedback line to the patient output terminal, thereby given rise to the possibility of the patient's coeliac tissue being burned by high frequency current.

It is accordingly the object of this invention to provide a high frequency surgical apparatus for an endoscope which can be operated efficiently and also assures the safe and reliable connection of a high frequency current feedback line to the patient output terminal of the surgical apparatus.

To attain the above-mentioned object, this invention provides a high frequency surgical apparatus wherein the endoscope connector is provided with a contact electrically connected to the endoscope metal section; a light supply unit is provided with a first contact connected to or detached from the endoscope connector, each time the connector is connected to or disengaged from the light supply unit; the light supply unit is further provided with a second contact electrically connected to the first contact; and this second contact and the patient output terminal of the high frequency surgical apparatus are connected together by a high frequency current feedback line.

Figure 2:
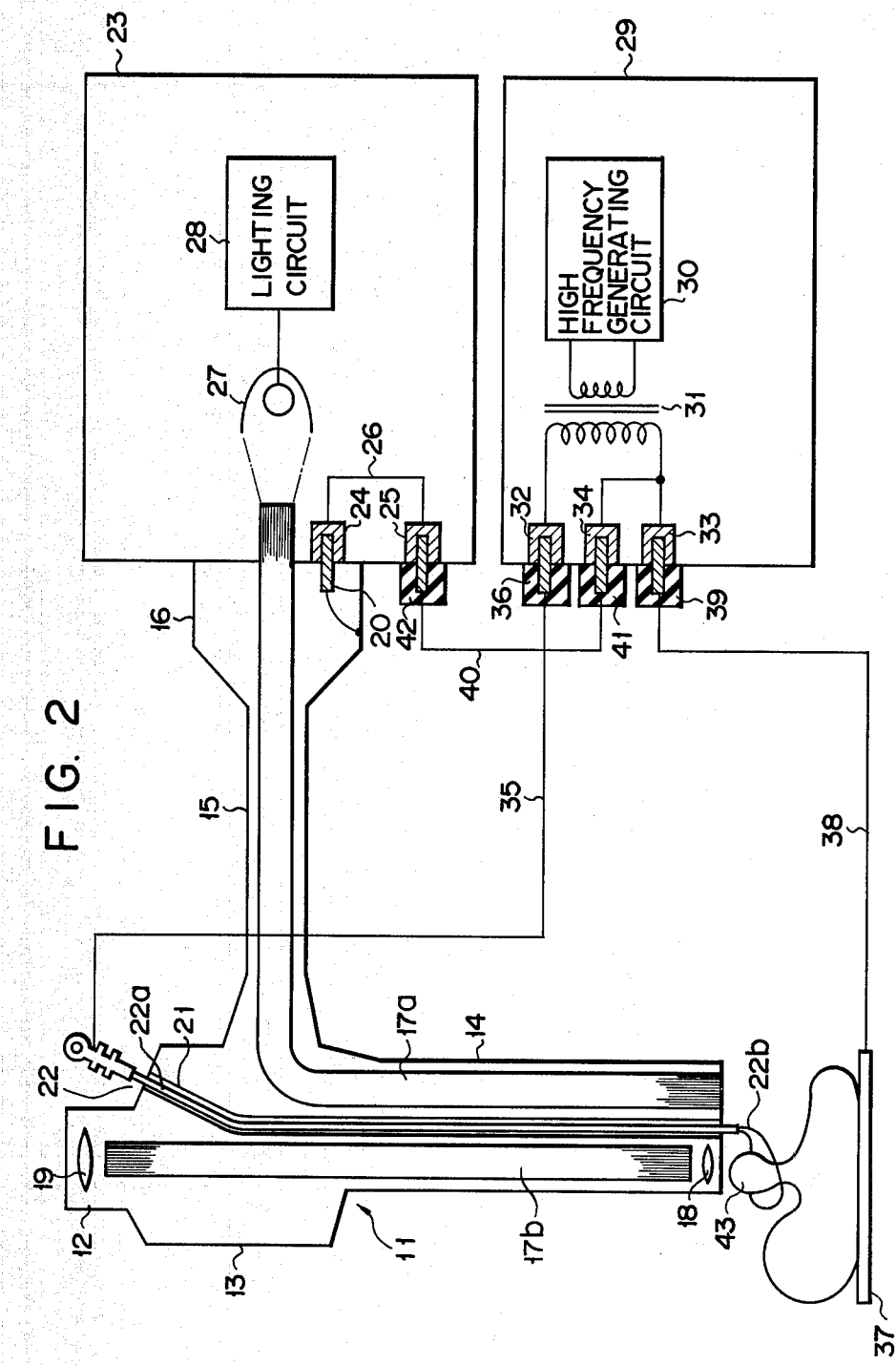

This invention can be more fully understood from the following detailed description when taken in conjunction with the accompanying drawings, in which:

FIG. 1 is an oblique view of an endoscope type high frequency surgical apparatus embodying this invention; and FIG. 2 schematically shows the internal arrangement of the endoscope type high frequency surgical apparatus of FIG. 1.

Referring to FIG. 1, an endoscope 11 comprises an eyepiece 12, control section 13, insertion section 14 and connector 16 fitted to the end of a universal cord 15. As shown in FIG. 2, a light guide 17a extends through the insertion section 14 starting with the connector 16 to the end of the insertion section 14. An image guide 17b extends from an object lens 18 set at the distal end of the insertion section 14 to an object lens 19 of the eyepiece 12. A forceps channel 21 extends from the control section 13 to the distal end of the insertion section 14. A sheath 22a of a diathermic snare assembly 22 is detachably fitted into the forceps channel 21. A diathermic snare wire 22b is inserted into the sheath 22a. A high frequency current feedback connection pin 20 is fixed to the end of the connector 16 in electrical connection to the metal section of the endoscope. Where the connector 16 is fitted to a light supply unit 23, then the connection pin 20 is connected to the first leaking high frequency current feedback terminal (simply referred to as "the first feedback terminal") 24 of the light supply unit 23. This first feedback terminal 24 is connected to a second leaking high frequency current feedback terminal (simply referred to as "the second feedback terminal") 25 through a lead 26. A light source 27 is so positioned as to face the light-incident end of the light guide 17. The lighting of the light source 27 is controlled by a lighting circuit 28.

A high frequency power supply source 29 is provided with a high frequency-generating circuit 30. The output terminal of this high frequency-generating circuit 30 is connected to the primary winding of a transformer 31. One end of a secondary winding of the transformer 31 is connected to an active output terminal 32, and the other end of the secondary winding is connected to another feedback terminal 34. The active output terminal 32 is detachably fitted to a plug 36 of an active output line 35, which is connected to the snare wire 22b of the diathermic snare assembly 22. A patient output terminal 33 is detachably connected to a plug 39 of a patient output line 38 connected to a patient electrode 37. The feedback terminal 34 is detachably connected to one plug 41 of a leaking high frequency current feedback line (simply referred to as "a feedback line") 40. The other plug 42 of the feedback line 40 is detachably connected to the second feedback terminal 25 of the light supply unit 23.

Where the above-mentioned endoscope type high frequency surgical apparatus arranged as described above is applied, then the connector 16 of the endoscope 11 is fitted to the light supply unit 23, causing the feedback connection pin 20 to be unfailingly connected to the first feedback terminal 24. The plugs 41 and 42 of the feedback line 40 are respectively connected to the feedback terminal 34 of the high frequency power supply source 29, and the second feedback terminal 25 of the light supply unit 23. As a result, the metal section of the endoscope 11 is electrically connected to the patient output terminal 33 of the high frequency power supply source 29. Where the plugs 36 and 39 are respectively connected to the active output terminal 32 and patient output terminal 33, then the active output terminal 32 and patient output terminal 33 are respectively electrically connected to the snare wire 22b and patient electrode 37. Where, under the above-mentioned condition, the high frequency-generating circuit 30 of the high frequency power supply source 29 is actuated, then a high frequency output from the high frequency-generating circuit 30 has its voltage stepped up by the transformer 31 to be applied between the active output terminal 32 and patient output terminal 33. Accordingly, high frequency current flows to the snare wire 22b through the active output plug 36 and active output line 35. When touched by the snare wire 22b, the patient's affected portion 43 is excised due to the tissue being subjected to discission. Since, in this case, the high frequency current generally has a frequency-generally ranging from 100 KHz to several MHz, part of the high frequency current unavoidably leaks to the metal section of the endoscope such as the insertion section 14. However, this leaking high frequency current is fed back to the patient output terminal 33 through the feedback connection pin 20, first feedback terminal 24, lead 26, second feedback terminal 25, plug 42, feedback line 40, plug 41 and feedback terminal 34. Even where particularly the metal part of the insertion section 14 of the endoscope 11 happens to be exposed to the outside due to the defect of the covering of the metal part, leaking high frequency current is prevented from flowing to the tissue of that portion of the coeliac wall which is contacted by the exposed metal part, thereby saving the tissue from burns.

Where the used endoscope 11 used is washed, or the endoscope 11 used is exchanged for another one, it is only required to release the endoscope connected 16 from the light supply unit 23. At this time, the feedback line need not be taken off. Where the endoscope 11 is again fitted to the light supply unit 23, it is only required to fit the connector 16 of the endoscope 11 to the light supply unit 23, making unnecessary the connection of the feedback line 40.

An endoscope type high frequency surgical apparatus embodying this invention has the advantages that as previously described, a high frequency current feedback line need not be connected or released where the endoscope is fitted to or removed from the light supply unit. Where endoscope, therefore, are repeatedly exchanged, the possibility is eliminated of the tissue of a patient's affected portion being burnt due to the negligence of connecting the high frequency current feedback line. The exchange of endoscope is carried out efficiently and the surgical operation by the subject high frequency surgical operation is quickly carried out.

What is claimed is:

1. An endoscope type high frequency surgical apparatus which comprises:
    an endoscope provided with a forceps channel, connector, metal section and high frequency current feedback contact which is mounted on the connector in electrical connection to the metal section;
    a light supply unit to which the endoscope connector is detachably fitted, and which is provided with a light source and a high frequency current feedback terminal detachably connected to the high frequency current feedback contact in accordance with the connection and removal of said endoscope connector;
    a high frequency powder supply source which generates high frequency surgical energy and is provided with an active output terminal and patient output terminal;
    a diathermic snare means inserted into the forceps channel of the endoscope in contact with the active terminal;
    patient electrode means connected to the patient output terminal; and
    high frequency current feedback means for electrically connecting the feedback terminal of the light supply unit to the paient output terminal of the high frequency power supply source.

2. The endoscope type high frequency surgical apparatus according to claim 1, wherein the high frequency current feedback means comprises:
    a first supplementary feedback terminal mounted on the light supply unit in electrical connection to the feedback terminal;
    a first plug detachably connected to the first supplementary feedback terminal;
    a second supplementary feedback terminal mounted on the high frequency power supply source in electrical connection to the patient output terminal;
    a second plug detachably connected to the second supplementary feedback terminal; and
    a feedback line for electrically connecting together the first and second plugs.

3. The endoscope type high frequency surgical apparatus according to claim 1 or 2, wherein the diathermic snare means comprises a sheath and a snare wire inserted into said sheath in electrical connection to the active output terminal.

4. The endoscope type high frequency surgical apparatus according to claim 1 or 2, wherein the high frequency power supply source comprises:
    a high frequency current-generating circuit;
    a transformer supplied with an output from said high frequency-generating circuit; and
    means for supplying an output from said transformer to the active output terminal and patient output terminal.

* * * * *